United States Patent
Andreev et al.

(10) Patent No.: US 8,306,309 B2
(45) Date of Patent: Nov. 6, 2012

(54) METHOD AND APPARATUS FOR DETECTING MECHANICAL DEFECTS IN A SEMICONDUCTOR DEVICE, PARTICULARLY IN A SOLAR CELL ARRANGEMENT

(75) Inventors: Thomas Andreev, Ottobrunn (DE); Claus Zimmermann, Munich (DE)

(73) Assignee: Astrium GmbH, Taufkirchen (DE)

( * ) Notice: Subject to any disclaimer, the term of this patent is extended or adjusted under 35 U.S.C. 154(b) by 533 days.

(21) Appl. No.: 12/526,435

(22) PCT Filed: Feb. 1, 2008

(86) PCT No.: PCT/DE2008/000180
§ 371 (c)(1),
(2), (4) Date: Dec. 10, 2009

(87) PCT Pub. No.: WO2008/095467
PCT Pub. Date: Aug. 14, 2008

(65) Prior Publication Data
US 2010/0150428 A1    Jun. 17, 2010

(30) Foreign Application Priority Data
Feb. 9, 2007    (DE) ................ 10 2007 007 140

(51) Int. Cl.
*G06K 9/00* (2006.01)
*G01R 31/26* (2006.01)
(52) U.S. Cl. .............. 382/145; 324/501; 250/214 R
(58) Field of Classification Search .............. 382/145; 250/214 R, 338.1, 339.14, 341.4; 324/501, 324/751, 752, 765
See application file for complete search history.

(56) References Cited

U.S. PATENT DOCUMENTS

| 5,334,844 | A  | * | 8/1994 | Pollard et al. .......... 250/330 |
| 6,225,640 | B1 | * | 5/2001 | Glenn et al. .......... 250/559.45 |
| 6,420,705 | B2 | * | 7/2002 | Chou et al. .......... 250/330 |
| 6,433,867 | B1 | * | 8/2002 | Esquivel .......... 356/237.2 |
| 6,528,794 | B1 | * | 3/2003 | Sato .......... 250/370.09 |
| 6,727,501 | B1 | * | 4/2004 | Fan et al. .......... 250/307 |
| 7,173,447 | B2 | * | 2/2007 | Yamashita et al. ....... 324/754.23 |

(Continued)

FOREIGN PATENT DOCUMENTS
DE    694 14 630 T2    6/1999
(Continued)

OTHER PUBLICATIONS

Y. Takahashi, et al., "Luminoscopy"—Novel Tool for the Diagnosis of Crystalline Silicon solar cells an Modules Utilizing Electroluminescence, Graduate School of Materials Science, Nara Institute of Science and Technology, 2006, pp. 924-927, XP-0022480020.

(Continued)

*Primary Examiner* — Sang Nguyen
(74) *Attorney, Agent, or Firm* — Crowell & Moring LLP (57) ABSTRACT

A process detects defects in a semiconductor device, particularly a solar cell or solar cell arrangement, having at least one pn junction in a semiconductor layer of a semiconductor material with an indirect band junction. A voltage is applied to the at least one pn junction to operate it in the transmitting direction; and the radiation behavior of the semiconductor layer generated by the applied voltage, at least for partial ranges of the semiconductor layer, is optically detected and automatically examined for essentially one-dimensional intensity changes in order to detect mechanical defects.

17 Claims, 3 Drawing Sheets

U.S. PATENT DOCUMENTS

| | | | |
|---|---|---|---|
| 7,601,941 B2 * | 10/2009 | Fuyuki | 250/214 R |
| 2005/0252545 A1 | 11/2005 | Nowlan et al. | |

FOREIGN PATENT DOCUMENTS

| | | |
|---|---|---|
| DE | 199 14 115 A1 | 11/1999 |
| DE | 102 48 504 A1 | 4/2004 |
| DE | 10 2005 002 651 B3 | 8/2006 |
| EP | 1 416 228 A1 | 5/2004 |
| EP | 1 416 228 B1 | 5/2004 |
| WO | WO 2006/076893 A1 | 7/2006 |
| WO | WO 2007/128060 A1 | 11/2007 |

OTHER PUBLICATIONS

International Search Report w/partial translation dated May 29, 2008 (nine (9) pages).

PCT/ISA/237 w/partial translation dated May 29, 2008 (twelve (12) pages).

* cited by examiner

METHOD AND APPARATUS FOR DETECTING MECHANICAL DEFECTS IN A SEMICONDUCTOR DEVICE, PARTICULARLY IN A SOLAR CELL ARRANGEMENT

This application is a national stage of PCT International Application No. PCT/DE2008/000180, filed Feb. 1, 2008, which claims priority under 35 U.S.C. §119 to German Patent Application No. 10 2007 007 140.1, filed Feb. 9, 2007, the entire disclosure of which is herein expressly incorporated by reference.

BACKGROUND AND SUMMARY OF THE INVENTION

The present invention relates to a process for detecting mechanical defects in a semiconductor device, such as a solar cell or solar cell arrangement.

In the case of solar generators for satellites, it is extremely important to detect mechanical defects in the solar cells before they are deployed in orbit. The reason is that mechanical or cell defects, such as ruptures, may continue to grow, principally as a result of the thermal cycles in orbit (90 eclipse phases per year in one geostationary orbit), and have an extremely negative effect on the reliability of the solar generators. It is therefore desired to achieve a 100% control of the cells with respect to mechanical defects before shipment (including all production steps), in order to exchange defective cells as early as possible and to avoid defective cells' being used in a solar generator. The same considerations of course also apply to terrestrial solar cells and modules even though, in contrast to the solar cells of a satellite in orbit, they can be exchanged more easily.

Currently, mechanical cell defects in solar cells made of indirect semiconductors, such as silicon, are detected by a visual cell inspection. That is, by looking at the solar cells under suitable illumination conditions, a trained eye can detect cell defects in reflected light, due to light effects caused by a slight vertical offset along the cell rupture. Since visual cell inspection is time-consuming and correspondingly expensive, however, efforts are being made to automate this process, for example, using phase-measuring deflectrometry. It has also been attempted to use external light of differing wavelengths in order to achieve a greater penetration depth, or to detect ruptures based on their effect on the transfer of heat, for example using thermographic methods. A survey of the detection of mechanical defects in solar cells can be found in the publication "Utilizing Lateral Current Spreading in Multijunction Solar Cells: An Alternative Approach to Detecting Mechanical Defects", C. G. Zimmermann, *J. Appl. Phys.* 100, 023714, 2006.

European Patent Document EP 1 416 288 B1 describes a process for optical detection of mechanical defects in semiconductor devices (particularly solar cell arrangements) which have at least one pn junction and at least one semiconductor layer made of a semiconductor material with a direct band junction. Operating the pn junction in the transmitting direction, affects the active radiation behavior, which can then be analyzed for the detection of mechanical defects. In contrast to the visual inspection process described above, the semiconductor device is thus not passively irradiated; rather, radiation behavior of the device itself is actively excited. The radiation behavior is affected by the radiating recombination of charge carriers at the direct band junction which are induced in the pn junction polarized in the transmitting direction. According to European Patent Document EP 1 416 288 B1 such detection is not possible in the case of semiconductor material such as germanium, with an indirect band junction, due to insufficient radiating recombination of charge carriers.

One object of the present invention therefore, is to provide an improved method and apparatus for detection of defects in semiconductor devices with an indirect semiconductor material, for example, silicon-based solar cells or solar cell arrangements.

This and other objects and advantages are achieved by the method and apparatus according to the present invention, which is based on the recognition that even indirect semiconductors such as silicon have an analyzable radiation behavior under certain conditions. The publication "Photographic Surveying of Minority Carrier Diffusion Length in Polycrystalline Silicon Solar Cells by Electroluminescence", T. Fuyuki, H. Kondo, T. Yamazaki, Y. Takahashi and Y. Uraoka, *Appl. Phys. Lett.* 86, 262108, 2005, indicates that the minority carrier diffusion length in polycrystalline silicon can be determined based on electroluminescence, and that therefore even indirect semiconductors supply sufficient analyzable electroluminescence. According to the invention, this recognition is now utilized in order to be able to use the process known from European Patent Document EP 1 416 288 B1, with a corresponding modification, also for the detection of mechanical defects in semiconductor devices with indirect semiconductor material.

By means of the invention, mechanical defects in a semiconductor device with a pn junction, which is based on an indirect semiconductor material (such as silicon), can therefore be detected by applying a voltage to this semiconductor device in the transmitting direction of the pn junction, so that the semiconductor device is excited to supply electromagnetic radiation. As a result of the indirect band junction, the resulting electroluminescence, however, is weaker by orders of magnitude than in direct semiconductors.

Optical detection of radiation emitted by the active layers in the semiconductor requires a suitable optical sensor, such as a CCD camera, which is adapted to the wavelength range of the determined radiation and, when integrated for an appropriate observation time, has a suitable sensitivity. For semiconductors based on Si or Ge (which are of considerable practical relevance), the emitted radiation will be in the infrared wavelength range. In this case, all visible light can be faded out by an infrared filter, so that relatively less sensitive detectors can also be used, and the detection of defects becomes possible in ambient light. In a more general case, suitable (band pass) filters can be used to isolate the radiation of a certain pn junction and to check only these semiconductor layers for defects. Optical detection in the sense of the present invention is particularly the local resolution of detected electromagnetic radiation emitted by the semiconductor device.

In this case, the radiation behavior of the semiconductor layer can be examined for abrupt, essentially one-dimensional intensity changes along the semiconductor layer, with detected changes of intensity being identified as mechanical defects of the semiconductor device. Such an analysis can be performed automatically by corresponding image processing systems or radiation intensity detectors. Therefore, not only is the global radiation behavior considered here qualitatively (radiation present or not present), but also the intensity course of the radiation behavior is examined locally along the semiconductor device or along the semiconductor layer with the indirect band junction. In this manner, local defects can be detected which impair the operability of the semiconductor device in certain partial ranges or in any other fashion. An abrupt essentially one-dimensional intensity change supports the conclusion that there is a mechanical defect, such as a rupture, of a semiconductor layer.

In principle, the process can also be used to detect local cloudiness, degradations or the like, for example, in cover glass and cover layers of solar cell. However, these may then have an effect, for example, as an intensity change of a two-dimensional nature in the radiation behavior and can be correspondingly detectable.

The present invention achieves a significant improvement of the detection of mechanical defects in planar semiconductor devices, which consist particularly of a semiconductor material with an indirect band junction, such as silicon. In contrast to visual cell inspection, which encounters its limits particularly in the case of texturized silicon solar cells, the detection rate for defects is almost 100% (in contrast to a visual detection rate of, as a rule, less than 50%). Furthermore, the inspection is not dependent on personnel, can be reproduced and permits an unambiguous defect documentation. In addition, the process saves time and can be automated.

According to an embodiment of the invention, a process is provided for detecting mechanical defects of a semiconductor device (particularly, a solar cell or solar cell arrangement) having at least one pn-junction in a semiconductor material characterized by an indirect band junction. For this purpose:
  a voltage is applied to the at least one pn junction to operate it in the transmitting direction;
  the radiation behavior of the semiconductor layer generated by the applied voltage, at least for partial ranges of the semiconductor layer, can be selected by means of a filter such, that either only the electromagnetic radiation of one or more pn junctions is detected, and/or that all visible ambient light is blocked;
  the filtered radiation behavior or, as required, also the unfiltered radiation behavior, is optically detected and analyzed;
  the radiation behavior of the semiconductor layer is automatically examined for abrupt, essentially one-dimensional intensity changes along the semiconductor layer, and detected intensity changes are identified as mechanical defects of the semiconductor device; and/or
  the integral is automatically determined the radiation intensity of at least a first partial range of a first semiconductor layer, and is automatically compared with an integral determined based on the radiation intensity of at least one comparison range of the same semiconductor layer or of a second semiconductor layer. Based on the result of an automatic comparison the first partial range is identified as defective or as free of defects.

According to another embodiment of the present invention, direct light incident on a surface of the semiconductor device can be filtered during the optical detection. This has the advantage of detecting and analyzing only that electromagnetic radiation which is emitted by the semiconductor device to which the conducting-state voltage is applied. Electromagnetic radiation which is, for example, reflected by the component and which is generated by light laterally incident on the surface of the semiconductor device, can thus be avoided.

According to another embodiment of the invention, the optical detection can take place within a time period of not more than two seconds. It was found that such a time period is suitable for taking high-resolution pictures of the Si-based semiconductor device for further analysis, using a conventional Si-CCD camera.

In addition, according to a further embodiment of the invention, a voltage for operating the pn junction in the transmitting direction can be applied which causes a current in a range of once or twice the short-circuit current intensity of the semiconductor device. It has been found that such a time period for taking high-resolution pictures of the Si-based semiconductor device is suitable for a further analysis for the detection, using a conventional Si-CCD camera.

According to an embodiment of the invention, the semiconductor material with the indirect band junction may comprise silicon, particularly polycrystalline silicon.

According to a further embodiment of the present invention, mechanical defects of a radiation-inactive layer of the semiconductor device can be detected automatically by examining the radiation behavior of an adjacent radiation-active semiconductor layer for abrupt, essentially one-dimensionally extending intensity changes along the semiconductor layer. Detected intensity changes are identified as mechanical defects of the radiation-inactive layer of the semiconductor device. By means of such an embodiment of the present invention, particularly in the case of tandem solar cells (or solar cells with two or more active layers), a rupture or a degradation of a non-radiating layer of the semiconductor device can also be detected by means of the method according to the invention, because the radiation behavior of the semiconductor device is influenced also by ruptures or degradations in the non-radiating layer.

In addition, according to a further embodiment of the invention, both mechanical defects and the electric effects thereof can be detected, Detection of mechanical defects is based on an analysis of the radiation behavior of the semiconductor device in a first wavelength range, while detection of electric effects is based on an analysis of the radiation behavior of the semiconductor device in a second wavelength range. Because even inactive layers influence the radiation behavior of the semiconductor device, they can also be examined for mechanical defects based on analysis of the radiation behavior of the semiconductor device in this manner.

According to a further embodiment of the present invention, a plurality of n semiconductor devices can be arranged in a series connection and/or parallel connection on a common semiconductor device carrier, and a voltage can be applied to the totality of the semiconductor devices which, in a series connection, corresponds to n-times the voltage (and, in a parallel connection, corresponds to n-times the current) for operation of a semiconductor device in the transmitting direction. As a result, particularly already preassembled solar cell panels or modules having several individual series-connected cells can be inspected.

According to a further embodiment of the invention, an arrangement for the detection of mechanical defects of a semiconductor device (particularly a solar cell or solar cell arrangement) may be provided with at least one pn junction in a semiconductor material characterized by an indirect band junction and at least one electrode connected to each of the respective p-conducting and n-conducting ranges of the semiconductor device, and further including,
  voltage supply connections to electrodes of the semiconductor device in order to permit a voltage supply for the operation of the pn junction in the transmitting direction;
  an arrangement for optical detection and analysis of the radiation behavior of the semiconductor layer generated by an applied voltage at least for partial ranges of the semiconductor, the arrangement comprising the following characteristics:
  an optional filter unit which can be selected only for detecting the radiation of one or more pn junctions and/or for blocking visible ambient light;
  an image data storage area for storing a radiation image of a semiconductor layer;

a first program storage area containing an image processing program, constructed for the automatic examination of at least one of the radiation images with respect to abrupt, essentially one-dimensional extending intensity changes and for the identification of the detected intensity changes as mechanical defects of the semiconductor device; and a second program storage area containing a program for the analysis of at least one of the radiation images with respect to electric effects of the mechanical defects.

In particular, the optical detection arrangement may also comprise an arrangement for filtering direct light incident on the surface of the semiconductor device, because the detection of the radiation emitted by the semiconductor device may be negatively influenced by reflections of light laterally incident on a surface of the semiconductor device.

In a further embodiment of the present invention, the optical detection arrangement may also be constructed to carry out the optical detection within a time period of not more than two seconds.

According to a further embodiment of the invention, the voltage supply may be constructed to apply an operating voltage to the pn junction in the transmitting direction via the voltage supply connections, which causes a current in a range of approximately once or twice the short-circuit current intensity of the semiconductor device.

Additional advantages and application possibilities of the present invention are contained in the following description in connection with the embodiments illustrated in the drawings.

BRIEF DESCRIPTION OF THE DRAWINGS

The terms and assigned reference symbols used in the attached list of reference symbols will be used in the description, in the claims, in the abstract and in the drawings.

DETAILED DESCRIPTION OF THE DRAWINGS

In the following, identical and/or functionally identical elements may be provided with the same reference symbols. The absolute values and measuring data indicated in the following are used only as examples, and do not limit the invention to such dimensions.

Figure 1:
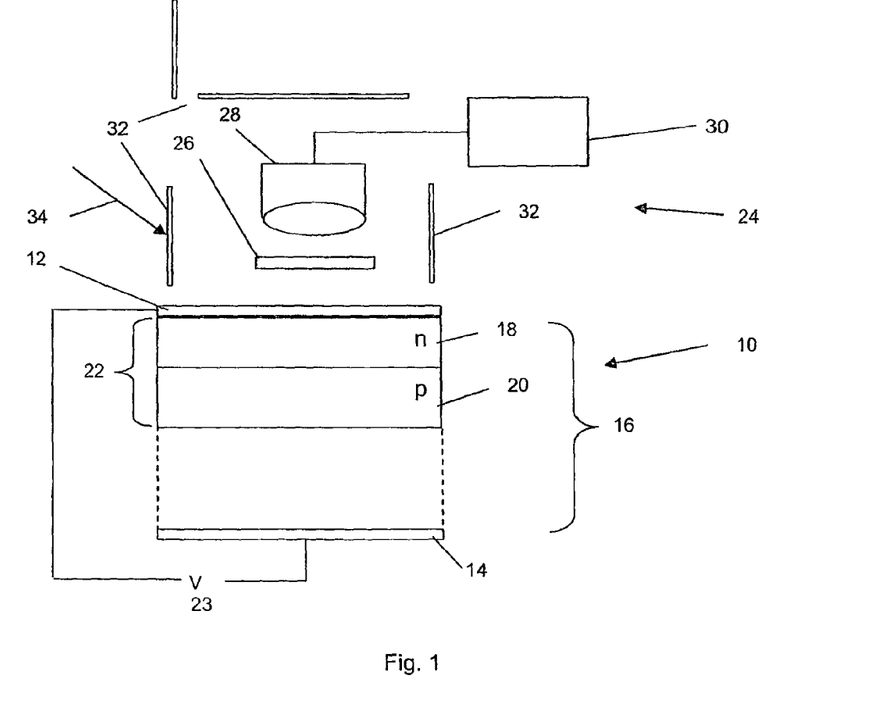
FIG. 1 is a diagram of a device for the detection of mechanical defects in a semiconductor device, according to an embodiment of the present invention.

FIG. 1 is a schematic diagram which illustrates the detection of mechanical defects in a semiconductor device according to an embodiment of the present invention. As shown there, a semiconductor device 10 comprises a top electrode 12 and a bottom electrode 14, with a semiconductor material 16 situated in-between. In this case, the semiconductor material 16 may be a semiconductor material with an indirect band junction, such as silicon (Si) or germanium (Ge). In this semiconductor material 16, an n-doped layer 18 is arranged above a p-doped layer 20, forming a pn junction 22.

Although not illustrated in FIG. 1, additional layers, such as an additional pn-junction or other inactive semiconductor layers, may be arranged between the pn junction 22 and the bottom electrode 14, which additional layers consist of either the same or a different semiconductor material (including another crystalline structure of the original semiconductor material). A reverse arrangement of the doping profiles is also conceivable (i.e., a p-doped layer disposed above an n-doped layer). Furthermore, a voltage V23 can be applied between the top electrode 12 and the bottom electrode 14.

In addition, FIG. 1 illustrates a recording unit 24 which has, for example, an infrared filter 26, an optical sensor, such as a CCD camera 28 (with a lens system connected on the input side) as well as an image analyzing unit 30 connected with the optical sensor (DDC camera) 28. In addition, FIG. 1 shows lateral screens 32 constructed for shielding a surface of the semiconductor device 10 (i.e., for example, the top surface of the top electrode 12) from lateral light 34.

When the semiconductor device 10 comprises a solar cell arrangement, the present invention utilizes the technical effect that, in response to incident light, a solar cell not only generates current, but also emits electromagnetic radiation (or electroluminescence occurs) when a voltage 23 is applied between the top electrode 12 and the bottom electrode 14 in such a manner that the pn junction 22 is operated in the transmitting direction. Although this effect occurs mainly in semiconductor materials with a direct band junction (radiating recombination of the charge carriers), it could also be determined that, in materials with an indirect band junction, a (significantly weaker) electroluminescence occurs, whose intensity is proportional to the minority carrier diffusion length.

Although ruptures or defects in the semiconductor device also influence the minority carrier diffusion length, it is particularly decisive for the process suggested according to the invention that ruptures or defects act as current drains and, connected with the transverse conductivity of the cell, macroscopically influence the lateral current distribution, and thus the spatial distribution of the electroluminescence of the cell, as illustrated in the publication "Utilizing Lateral Current Spreading in Multijunction Solar Cells: An Alternative Approach to Detecting Mechanical Defects", C. G. Zimmermann, *J. Appl. Phys.* 100, 023714, 2006. Thus, conclusions can be drawn with respect to such ruptures or defects from the detection of the spatial distribution of the emitted electroluminescence.

In semiconductor devices based on Si and Ge, it should be noted that this electroluminescence takes place in the infrared spectral region (i.e., electromagnetic radiation with a wavelength of more than 800 nm). Therefore, in order to fade out electromagnetic radiation of other spectral regions, an infrared filter 26 is used with the recording unit 24, to focus the sensitivity of the recording sensor 28 (which, as illustrated in FIG. 1, may, for example be a conventional Si-CCD camera) especially on the spectral region that is of interest, filtering other disturbing spectral regions. The lateral screens 32 thus prevent the infrared fraction of laterally incident light 34 from being reflected by the surface of the semiconductor device 10 into the recording unit 28, which would falsify the recorded image.

The recording unit 28 may also be equipped with other filter combinations in order to selectively detect the electroluminescence of one or more pn junctions.

Figure 2:
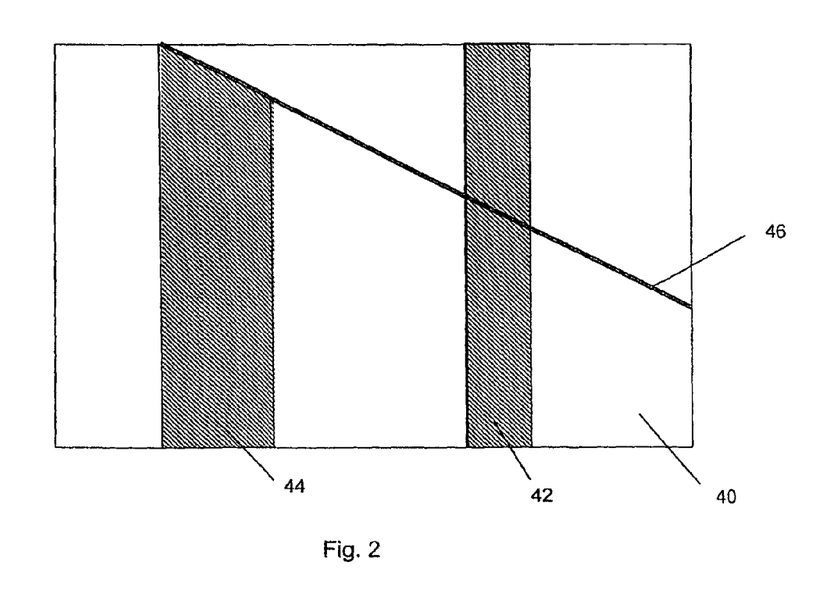
FIG. 2 illustrates the radiation behavior of a defective semiconductor device from its surface.

FIG. 2 is a schematic representation of a conceivable picture of the surface of the semiconductor device 10 illustrated in FIG. 1. The rupture 46 in the pn junction 22, clearly recognizably, appears as an essentially one-dimensional intensity reduction of the electroluminescence radiation of the cell (light regions 40). The rupture is correspondingly illustrated as a black line in FIG. 2. There is also the possibility that the rupture 46 extends, for example, in an (inactive) layer arranged below the pn junction and that this rupture has a negative effect on the crystalline structure in the pn junction 22, so that also a rupture in an inactive layer can be recognized by means of the suggested approach.

These abrupt, essentially one-dimensional intensity changes very easily permit an automatic recognition of defects by familiar image processing systems. Furthermore, the process according to the invention also makes it possible to detect electric effects associated with a rupture. Thus, for example, the complete area 42 is electrically impaired by the rupture and is characterized by a reduced electroluminescence. In area 44, such impairment occurs only in the area below the rupture 46. By means of the process according to the invention, the radiation behavior of the solar cell arrangement can be optically analyzed in a simple manner so that a direct, unambiguous and reproducible conclusion can be drawn regarding defects in the solar cell arrangement.

Figure 3:
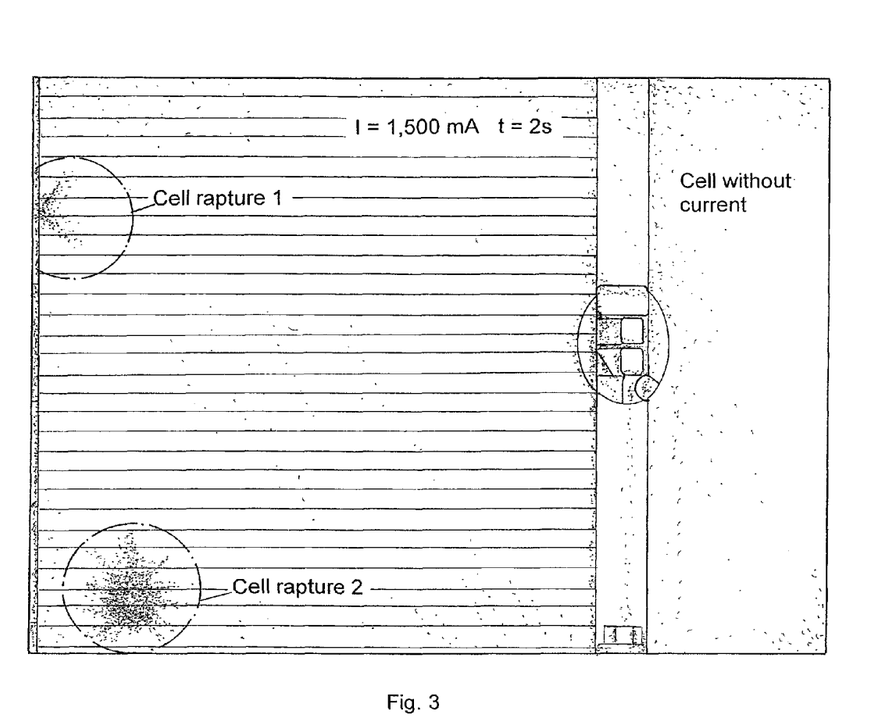
FIG. 3 is a photograph of an example of a defective silicon solar cell using an embodiment of the approach according to the invention.

FIG. 3 is a photo of an example of such an electroluminescence picture of a silicon solar cell, in which a corresponding voltage was applied to operate the respective pn junctions in the transmitting direction. In this case, the solar cell was acted upon by a current of I=1,500 mA for a time period of t=2 s. Thus, under the listed parameters, the cell ruptures called "cell rupture 1" and "cell rupture 2" became visible in a highly resolved manner. For the purpose of comparison, a solar cell without an external forward current is situated on the right margin.

Figure 4:
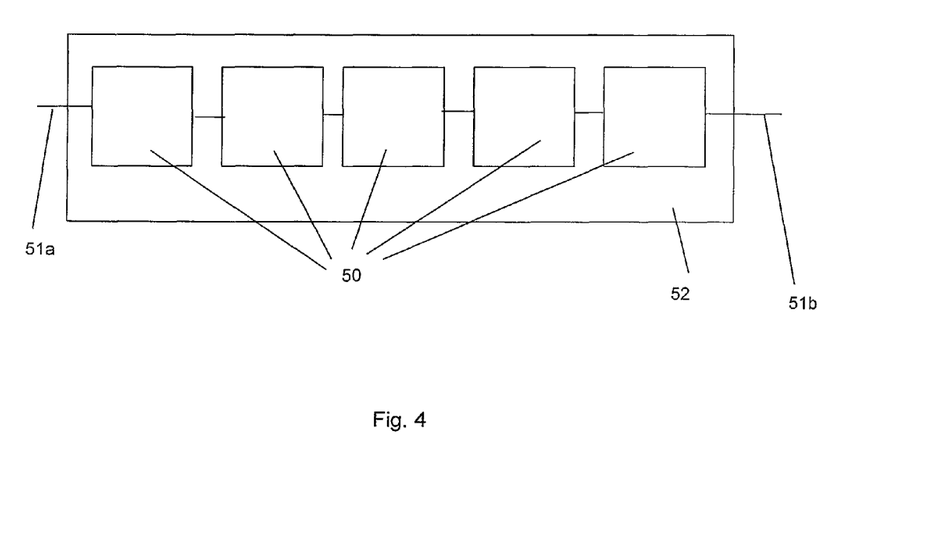
FIG. 4 is a schematic view of an arrangement of several solar cells forming a string according to an embodiment of the present invention.

FIG. 4 shows several solar cell arrangements 50 which are combined to form a string, and each of which consist, for example, of one semiconductor device 10 such as illustrated in FIG. 1. In this case, the individual solar cell arrangements 20 are connected in series via their electrodes 51a and 51b respectively. The solar cell arrangements 50 are mounted on a common carrier 52. In the case of an arrangement of n solar cells 50, when a voltage is now applied to the entire string, which voltage amounts to n times that which is necessary to switch a single solar cell arrangement 50 in the transmitting direction, the entire string of solar cells can be tested in one operation.

Figure 5:
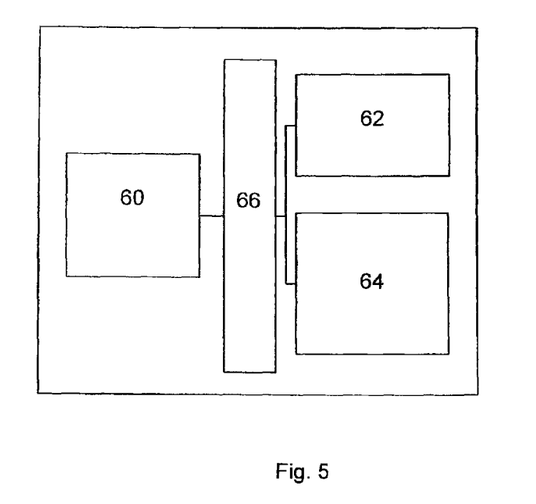
FIG. 5 is a schematic view of an image processing arrangement.

FIG. 5 is a schematic diagram which shows the essential functionalities of a possible embodiment of the image processing unit 30. It includes an image data storage area 60 for storing a radiation image of the semiconductor layer 10 (or of the pn junction 22), a program storage area 62 containing an image processing program configured for the automatic examination of the radiation image for abrupt, essentially one-dimensionally extending intensity changes for identifying the detected intensity changes as mechanical defects of the semiconductor device, and a second program storage area 64 containing a program for analyzing the radiation image with respect to electric effects of the mechanical defects. The two programs can be executed by a computer unit 66 which, with respect to data, is connected with the individual storage areas 60 to 64.

Figure 6:
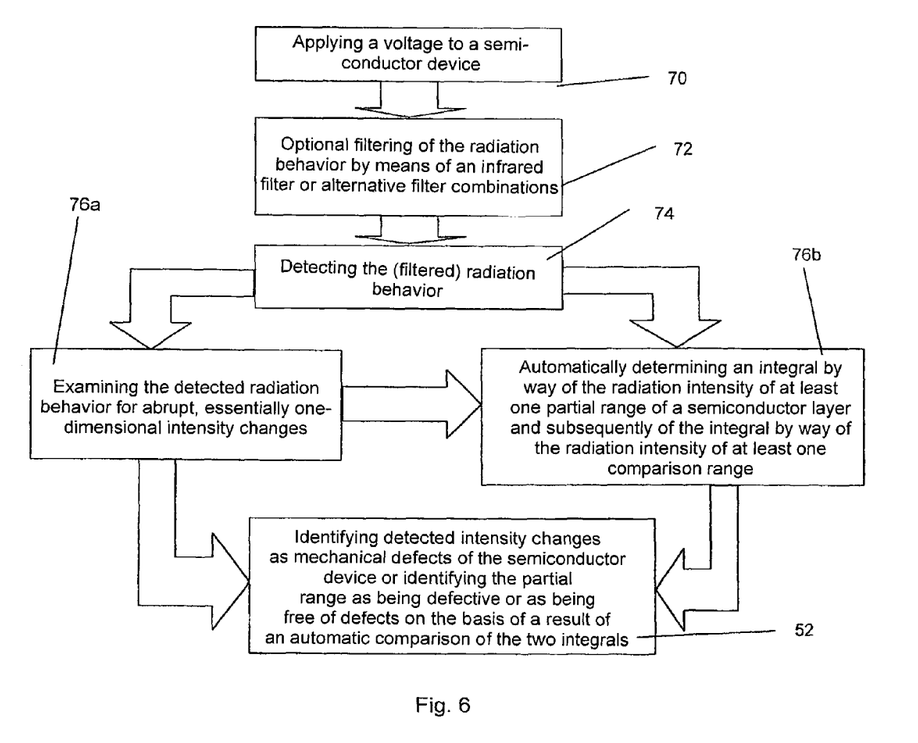
FIG. 6 is a flow chart of an embodiment of the process according to the invention.

FIG. 6 is a flow chart of an embodiment of the process according to the invention. In a first process step 70, a voltage is applied to the pn junction of the semiconductor device (having at least one pn junction in a semiconductor material with an indirect band junction), in the transmitting direction. In a second process step 72, the radiation behavior of the semiconductor layer (in the case of an Si semiconductor device) generated by the applied voltage is filtered, at least for partial ranges of the semiconductor layer, by means of an infrared filter, such that electromagnetic radiation in the spectral region with a lower wavelength than infrared is blocked. From a general aspect, other filter combinations may of course be meaningful.

Subsequently, the filtered radiation behavior will be optically detected in a third process step 74, for example, by means of a CCD camera. Finally, the detected radiation behavior is analyzed in a last process step 76a. In particular, the radiation behavior of the semiconductor layer is automatically examined for abrupt, essentially one-dimensional changes of intensity along the semiconductor layer; and detected intensity changes are identified as mechanical defects of the semiconductor device (process step 78).

As an alternative or in addition, in a further process step 76b, the integral can be automatically determined by way of the radiation intensity of at least a first partial range of a first semiconductor layer. Subsequently, the integral can be determined by way of the radiation intensity of at least a comparison range of the same semiconductor layer or a second semiconductor layer. Finally, based on the result of an automatic comparison of the two integrals, the first partial range can be identified as being defective or as being free of defects (process step 78).

Summarizing, it should be noted that it could be shown, for example, by means of a conventional CCD camera (like the commercially available Sony XCD-SX910 SiCCD camera) and an infrared filter that, by applying a current, for example, in the order of magnitude of $1-2 \times Isc$ (=short-circuit current of the cell) and exposure times of 1-2 s, high-resolution pictures of the cell ruptures in silicon solar cells can be taken, as illustrated in FIG. 3. The selected parameters afford good compatibility between the process according to the invention, and the demands of production: The selected current range is uncritical for the cell and does not damage the latter. The exposure times of 1-2 s ensure a fast inspection of all cells. The camera uses a standard Si-CCD detector and therefore has a reasonable price, especially since no additional measures are required, such as a cooling of the camera. Visible ambient light is blocked by the infrared filter; only a shading of direct light incident on the cell can then take place.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

LIST OF REFERENCE SYMBOLS

10 Semiconductor device
12 Top electrode
14 Bottom electrode
16 Semiconductor material
18 n-doped layer
20 p-doped layer
22 pn junction
23 Voltage V for operating the semiconductor device in the transmitting direction
24 Recording unit
26 Infrared filter
28 Optical sensor, CCD camera
30 Analyzing unit
32 Lateral screens
34 Lateral light, incident light 40 Luminescent surface areas of the semiconductor device
42, 44 Areas of the semiconductor with reduced electroluminescence
46 Rupture, mechanical defect
50 Semiconductor devices in a module arrangement
51a, 51b Connecting electrodes of the module
52 Semiconductor device carrier
60 Image data storage area
62 First program storage area
64 Second program storage area
66 Computer unit
70 Step of applying a voltage to the semiconductor device
72 Step of filtering the radiation behavior by means of an infrared filter
74 Detection of the filtered radiation behavior
76a Examination of the detected radiation behavior for abrupt, essentially one-dimensional intensity changes
76b Automatic determination of an integral by way of the radiation intensity of at least a first partial range of a first semiconductor layer and subsequently of the integral by way of the radiation intensity of at least a comparison range of the same semiconductor layer or of a second semiconductor layer
78 Identification of detected intensity changes as mechanical defects of the semiconductor device or identification of the first partial range as being defective or as being free of defects on the basis of a result of an automatic comparison of the two integrals

The invention claimed is:

1. A method for detecting mechanical defects in a semiconductor device, having at least one pn junction in a semiconductor layer formed of a semiconductor material that is characterized by an indirect band junction; said method comprising:
  applying to the at least one pn junction, a voltage for operating the pn junction in a transmitting direction;
  optically detecting and analyzing radiation behavior of the semiconductor layer generated by the applied voltage, at least for partial ranges of the semiconductor layer; and
  performing at least one of the following,
    i) automatically examining the radiation behavior of the semiconductor layer for abrupt substantially one-dimensional changes of intensity along the semiconductor layer, and identifying detected intensity changes as mechanical defects of the semiconductor device by an image processing unit; and
    ii) automatically integrating radiation intensity of at least a first partial range of a first semiconductor layer, automatically comparing a resulting integral with an integral of radiation intensity of at least one comparison range of the same semiconductor layer or of a second semiconductor layer, and identifying the first partial range as either defective or free of defects, based on a result of an automatic comparison of the two integrals, by the image processing unit.

2. The method according to claim 1, wherein the semiconductor device is a solar cell arrangement.

3. The method according to claim 1, wherein:
  the semiconductor material is Si; and
  an infrared filter is used for optical detection of the radiation behavior of the semiconductor layer, so that an electromagnetic radiation in the spectral region with a wavelength lower than infrared is blocked.

4. The method according to claim 1, wherein electroluminescence of at least one pn junction is selected by filter combinations adapted to the semiconductor material.

5. The method according to claim 1, wherein direct light incident on a surface of the semiconductor device is shaded during the detection.

6. The method according to claim 1, wherein the optical detection takes place within a time period of not more than two seconds.

7. The method according to claim 1, wherein a voltage for operating the pn junction in the transmitting direction is applied which causes a current in a range of approximately once to twice a short-circuit current intensity of the semiconductor device.

8. The method according to claim 1, wherein the semiconductor material comprises one of silicon and polycrystalline silicon.

9. The method according to claim 1, wherein:
  mechanical defects of a radiation-inactive layer of the semiconductor device are detected indirectly by the image processing unit;
  radiation behavior of an adjacent radiation-active semiconductor layer is automatically examined for abrupt substantially one-dimensional changes of intensity changes along the semiconductor layer by the image processing unit; and
  detected intensity changes are identified as mechanical defects of the radiation-inactive layer of the semiconductor device by the image processing unit.

10. The process according to claim 1, wherein:
  a combined detection of mechanical defects and the electrical effects of the mechanical defects are performed by the image processing unit;
  detection of mechanical defects by the image processing unit is based on an analysis of the radiation behavior of the semiconductor device in a first wavelength range; and
  detection of electric effects by the image processing unit is based on an analysis of the radiation behavior of the semiconductor device in a second wavelength range.

11. The method according to claim 1, wherein:
  a plurality of n semiconductor devices is arranged in a series connection on a common semiconductor device carrier; and
  a voltage is applied to the totality of the semiconductor devices which voltage corresponds to n-times the voltage necessary to operate a semiconductor device in a transmitting direction.

12. The method according to claim 1, wherein:
  a plurality of n semiconductor devices is arranged in a parallel connection on a common semiconductor device carrier; and
  a voltage is applied to the totality of the semiconductor devices which voltage causes n-times the current that is necessary to operate a semiconductor device in the transmitting direction.

13. Apparatus for detection of mechanical defects of a semiconductor device having at least one pn junction formed in a semiconductor material that is characterized by an indirect band junction; said apparatus comprising:
  at least one electrode which is connected with a p-conducting range of the semiconductor device;
  at least one electrode, which is connected with the n-conducting range of the semiconductor device;
  voltage supply connections which are connected with said electrodes for supplying a voltage sufficient to operate the pn junction in a transmitting direction;
  a device for optical detection and analysis of radiation behavior of the semiconductor layer generated by the supplied voltage, at least for partial ranges of the semiconductor layer, said optical detection device comprising a filter unit which is constructed such that at least one of i) an electromagnetic radiation in the spectral region with a lower wavelength than infrared is blocked; and ii) the radiation of one or more pn junctions is isolated;

an image data storage area for storing a radiation image of a semiconductor layer;

a first program storage area containing an image processing program configured for automatic examination of a radiation image with respect to abrupt, substantially one-dimensional intensity changes and for identification of detected intensity changes as mechanical defects of the semiconductor device; and a second program storage area containing a program for analysis of the radiation image with respect to electric effects of identified mechanical defects.

14. The apparatus according to claim 13, wherein the device for optical detection and analysis also comprises an arrangement for blocking direct light from impinging on a surface of the semiconductor device.

15. The apparatus according to claim 13, wherein the device for optical detection and analysis is configured to carry out the optical detection within a time period of not more than two seconds.

16. The apparatus according to claim 13, wherein:

the voltage supply is constructed for applying a voltage for operating the pn junction in the transmitting direction by way of the voltage supply connections; and said voltage causes a current in a range of approximately once to twice a short-circuit current intensity of the semiconductor device.

17. The apparatus according to claim 13, wherein the semiconductor device comprises one of a solar cell and a solar cell arrangement.

* * * * *